US012658313B2

(12) United States Patent
Hansen et al.

(10) Patent No.:    US 12,658,313 B2
(45) Date of Patent:        Jun. 16, 2026

(54) SYSTEMS AND METHODS FOR CONFIGURING REGIONAL SETTING(S) ON AN ULTRASOUND IMAGING DEVICE

(71) Applicant: Clarius Mobile Health Corp., Vancouver (CA)

(72) Inventors: Trevor Stephen Hansen, North Vancouver (CA); Kris Dickie, Vancouver (CA); Dongkang Li, Coquitlam (CA)

(73) Assignee: Clarius Mobile Health Corp., Vancouver (CA)

( * ) Notice: Subject to any disclaimer, the term of this patent is extended or adjusted under 35 U.S.C. 154(b) by 0 days.

(21) Appl. No.: 18/808,711

(22) Filed:    Aug. 19, 2024

(65)                Prior Publication Data

US 2025/0322944 A1      Oct. 16, 2025

Related U.S. Application Data

(60) Provisional application No. 63/634,854, filed on Apr. 16, 2024.

(51) Int. Cl.
G16H 40/67          (2018.01)
G16H 40/40          (2018.01)

(52) U.S. Cl.
CPC ............. G16H 40/40 (2018.01); G16H 40/67 (2018.01)

(58) Field of Classification Search
None
See application file for complete search history.

(56)                References Cited

U.S. PATENT DOCUMENTS

| | | | |
|---|---|---|---|
| 6,484,029 B2 | 11/2002 | Hughes et al. | |
| 9,654,965 B2 | 5/2017 | Kennedy et al. | |
| 9,992,326 B1 | 6/2018 | Koller et al. | |
| 2009/0046317 A1* | 2/2009 | Yoo | H04W 4/02 |
| | | | 358/1.15 |
| 2011/0066550 A1* | 3/2011 | Shank | G06Q 20/40 |
| | | | 701/469 |
| 2017/0227660 A1* | 8/2017 | Zhang | H04W 12/50 |
| 2020/0028929 A1* | 1/2020 | Xavier | G16H 80/00 |

* cited by examiner

*Primary Examiner* — John A Pauls

(74) *Attorney, Agent, or Firm* — Julian Ho; Susan Ben-Oliel

(57)                ABSTRACT

A method for configuring at least one regional setting on an ultrasound imaging device comprises the ultrasound imaging device receiving location data from a mobile device, via a connection therebetween and the mobile device employing the location data, assigned to the ultrasound imaging device, to configure the at least one regional setting on the ultrasound imaging device.

20 Claims, 12 Drawing Sheets

200

100

112     110

130

140

112     110

110

112

102

200

300

Receive location data from a mobile device via a connection therebetween — 310

Employ the location data, by the mobile device, assigned to the ultrasound imaging device to configure a regional setting on the ultrasound imaging device — 320

400B 402  404

410

430  BOB SMITH         ULTRASOUND APP  414

432  MOUNT SINAI HOSPITAL

SCANNERS

ID: ABC123  420

Available Features:  422
AI+, Feature Express

412

Location: Canada  424

500

Receive location data from a mobile device — 510

Assign location data to ultrasound imaging device — 512

Identify one or more device features based on location data assigned to ultrasound imaging device — 514

Activate one or more device features for use on ultrasound imaging device — 516

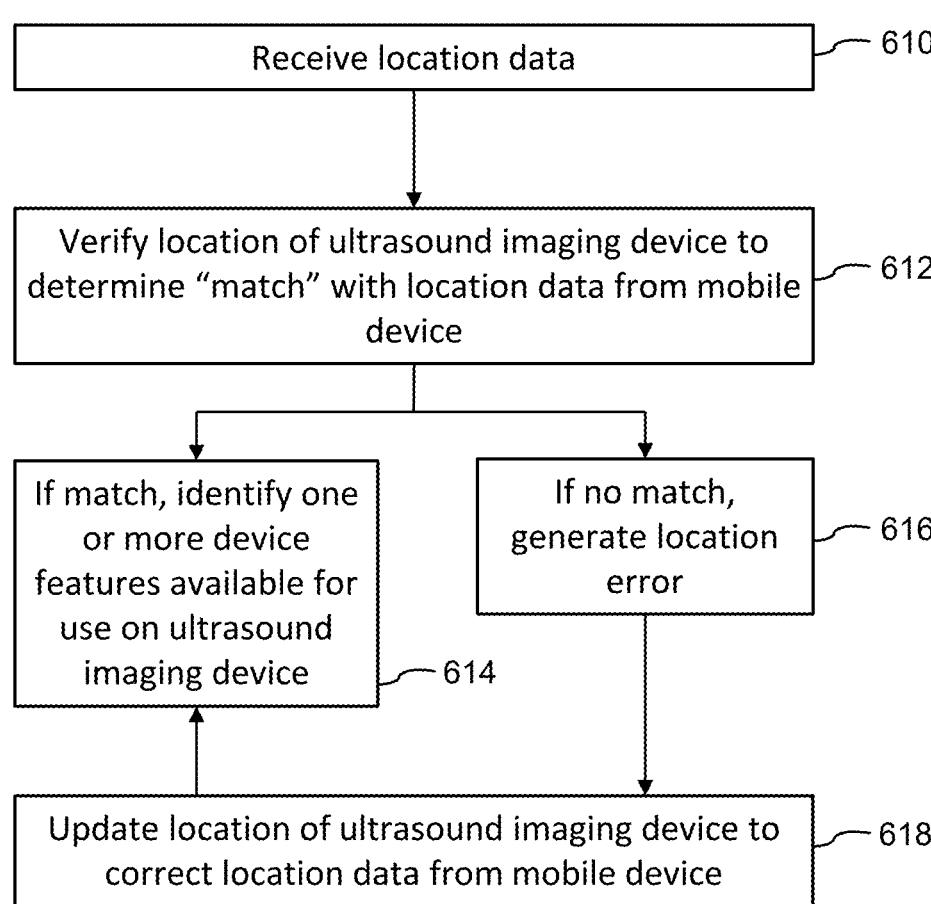
FIG. 6

700

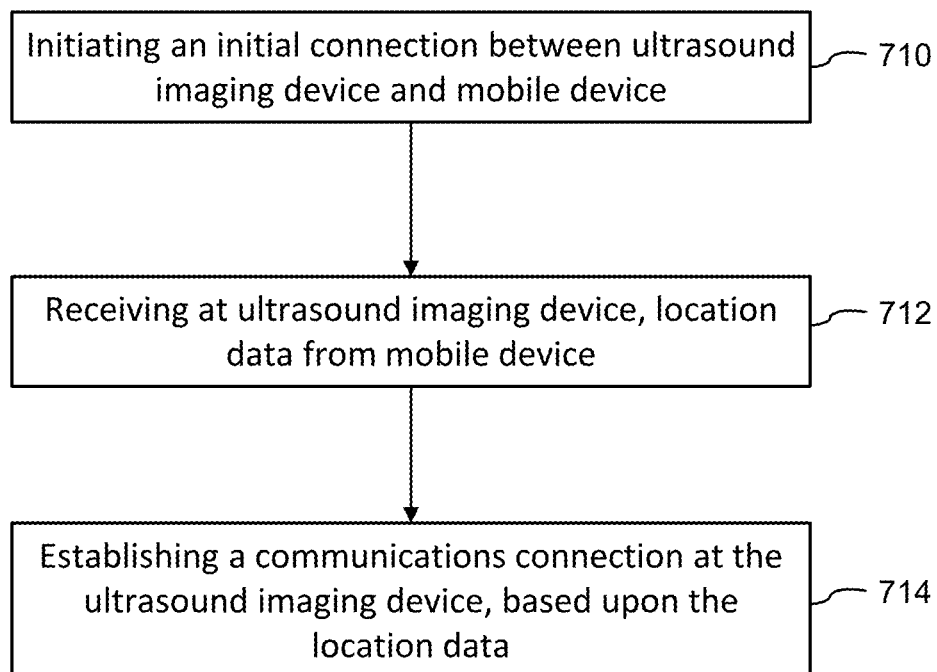

```
┌─────────────────────────────────────────────┐
│  Initiating an initial connection between     │──── 710
│  ultrasound imaging device and mobile device  │
└─────────────────────────────────────────────┘
                      │
                      ▼
┌─────────────────────────────────────────────┐
│  Receiving at ultrasound imaging device,      │──── 712
│  location data from mobile device             │
└─────────────────────────────────────────────┘
                      │
                      ▼
┌─────────────────────────────────────────────┐
│  Establishing a communications connection     │
│  at the ultrasound imaging device, based      │──── 714
│  upon the location data                       │
└─────────────────────────────────────────────┘
```

FIG. 7

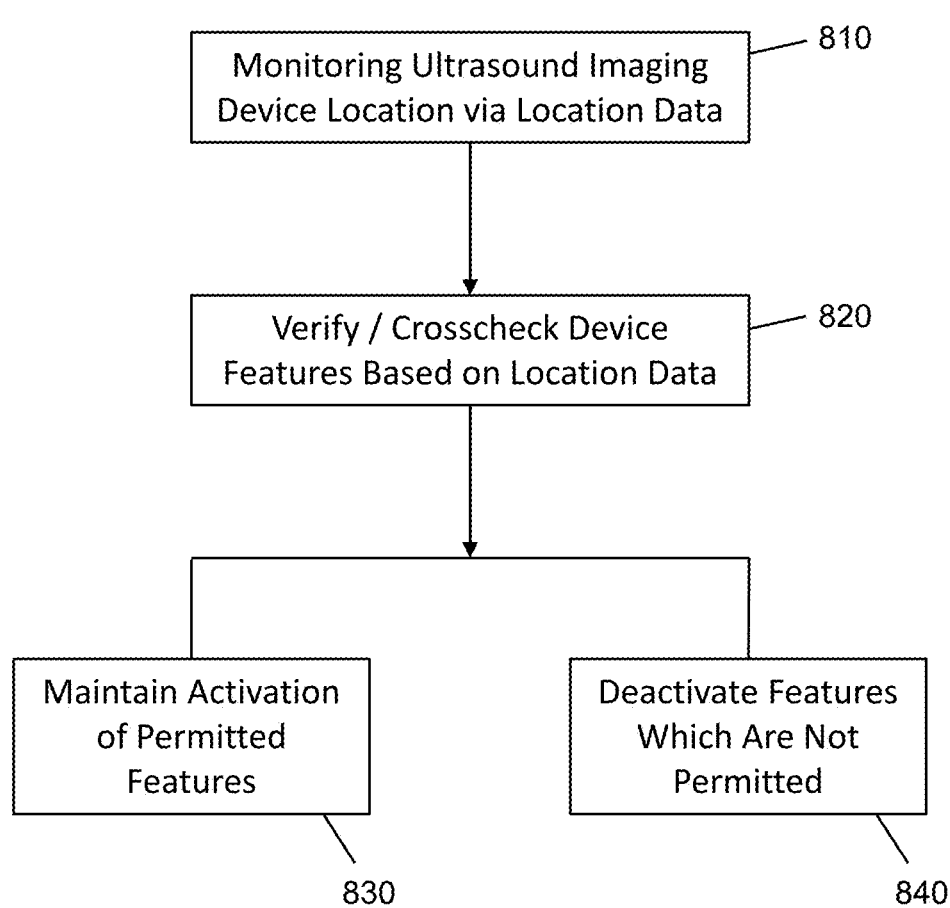
FIG. 8

900

Configuring Regional Setting of Ultrasound
Imaging Device via Location Data —— 910

Identifying One or More Device Features
Available and/or Limitations of Available Device
Features —— 920

Activate
Available Device
Features in Full

930

Activate
Available Device
Features with
Limitations

940

Decline the
Activation of
Device Features

950

Monitoring via
Step 610 in Fig. 6

960

SYSTEMS AND METHODS FOR CONFIGURING REGIONAL SETTING(S) ON AN ULTRASOUND IMAGING DEVICE

CROSS-REFERENCE TO RELATED APPLICATION(S)

This application claims the benefit of U.S. Provisional Patent Application No. 63/634,854, filed Apr. 16, 2024, and titled "SYSTEMS AND METHODS FOR CONFIGURING REGIONAL SETTING(S) ON AN ULTRASOUND IMAGING DEVICE". The complete disclosure of U.S. Provisional Patent Application No. 63/634,854 is incorporated herein by reference for all purposes.

FIELD OF THE INVENTION

The present disclosure relates generally to ultrasound imaging, and in particular, systems and methods for configuring regional setting(s) on an ultrasound imaging device.

BACKGROUND OF THE INVENTION

Ultrasound imaging systems are an important tool for diagnosis and therapy in a wide range of medical applications. Conventionally, ultrasound systems were large, expensive units used only in radiology departments by highly trained specialists. To improve portability and usability and enable ultrasound to be used at the point-of-care and by more users, various attempts have been made to reduce the size and cost of these systems and avoid the ergonomically troublesome cables that are typically used to attach handheld transducers to processing hardware.

In part to facilitate the reduction in size of these systems and to increase mobility, ultrasound imaging systems can include a mobile device that communicates with an ultrasound imaging device via a wired connection and/or wireless connection. Often in such systems, until the ultrasound imaging device is initialized with the mobile device, their functionality can be limited due to security risks and regulatory constraints.

For example, ultrasound imaging systems are typically sold and delivered with at least some device features that are deactivated by default. Only upon initialization at an intended location of use are the available device features activated. Whether the device features are activated can depend on various factors, including the jurisdiction of the location of use since regulatory restrictions may affect the availability of some device features and/or whether licenses for device features are obtained for that use.

Traditional methods of determining which device features should be activated can involve receiving a manual input from the user at the location of use but this is a manual process that relies on the user input to be accurate. Other manners of obtaining location information can involve obtaining location information from a wireless router or beacons at the location of intended use or a Global Positioning System (GPS). However, wireless routers and beacons are typically manually configured, and the settings may not be accurate. There are also possible technical workarounds, such as through use of virtual private networks (VPNs), that can mask the actual current location. In some cases, GPS data may not be consistently available—such as in rural or indoor environments.

There is a need for ultrasound imaging systems that configure regional setting(s) seamlessly upon initialization of the ultrasound imaging systems without depending on location data provided manually by users and/or unreliable sources.

The embodiments discussed herein may address and/or ameliorate at least some of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF THE DRAWINGS

Non-limiting examples of various embodiments of the present disclosure will next be described in relation to the drawings, in which:

FIG. 6 is a flowchart diagram showing steps of a method for verifying location of an ultrasound imaging device, in accordance with at least one embodiment of the present invention;

FIG. 7 is a flowchart diagram showing steps of a method for initiating an initial connection between an ultrasound imaging device and a mobile device, in accordance with at least one embodiment of the present invention;

FIG. 8 is a flowchart diagram showing steps of a method for maintaining and deactivating features, in accordance with at least one embodiment of the present invention;

Figure 1:
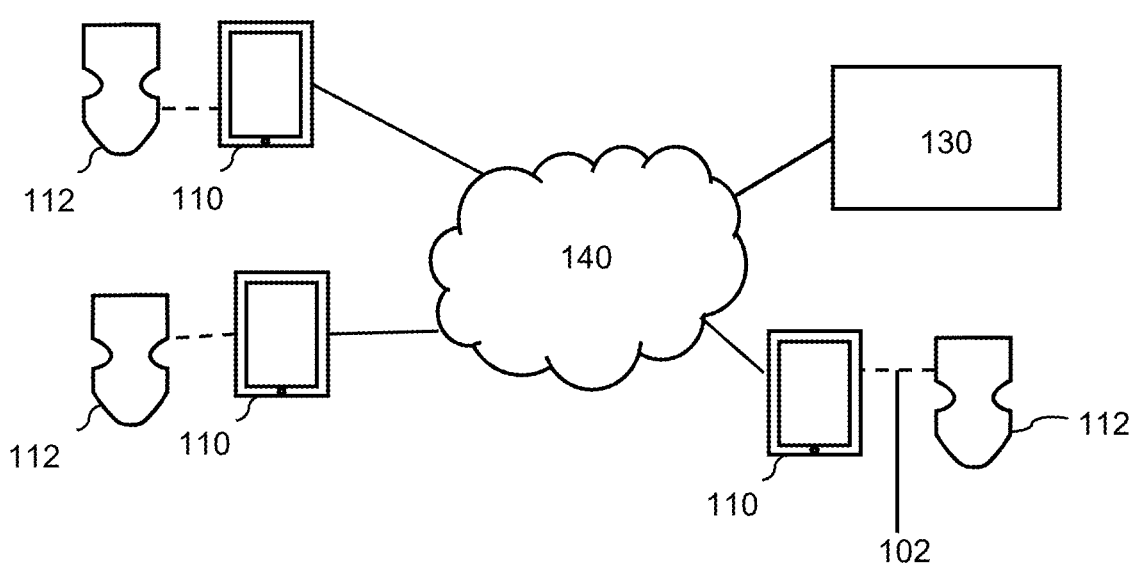
FIG. 1 is a schematic diagram of a system with multiple ultrasound scanners, according to an embodiment of the present invention.

Unless otherwise specifically noted, articles depicted in the drawings are not necessarily drawn to scale.

DETAILED DESCRIPTION OF THE INVENTION

A. Glossary

The term "communications network" and "network" can include both a mobile network and data network without limiting the term's meaning, and includes the use of wireless (e.g. 2G, 3G, 4G, 5G, WiFi®, WiMAX®, Wireless USB (Universal Serial Bus), Zigbee®, Bluetooth® and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "module" can refer to any component in this invention and to any or all of the features of the invention without limitation. A module may be a software, firmware or hardware module (or part thereof), and may be located or operated within, for example, in the ultrasound scanner, a display device or a server.

The term "multi-purpose electronic device" or "display device" or "computing device" or "off-the-shelf display computing device" or "mobile device" is intended to have broad meaning and includes devices with a processor communicatively operable with a screen interface, for example, such as, laptop computer, a tablet computer, a desktop computer, a smart phone, a smart watch, spectacles with a built-in display, a television, a bespoke display or any other display device that is capable of being communicably connected to an ultrasound scanner. Such a device may be communicatively operable with an ultrasound scanner and/ or a cloud-based server (for example via one or more communications networks). Such device may be combined with processor, non-transitory memory, and/or user input device in a shared electronic device, or there may be peripheral display devices which may comprise a monitor, touchscreen, projector, or other display device known in the art, which may enable a user to view ultrasound images produced by an ultrasound imaging system, and/or interact with various data stored in non-transitory memory.

The term "operator" (or "user") may (without limitation) refer to the person that is operating an ultrasound scanner (for example, a clinician, medical personnel, a sonographer trainer, a student, a vet, a sonographer/ultrasonographer and/or ultrasound technician). This list is non-exhaustive.

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "system" when used herein, and not otherwise qualified, may include an ultrasound scanner and a multi-purpose electronic device/display device; and/or an ultrasound scanner, multi-purpose electronic device/display device and a server. The system may include one or more applications operating on a multi-purpose electronic device/ display device to which the ultrasound scanner is communicatively connected.

The term "ultrasound transducer" (or "probe" or "ultrasound probe" or "transducer" or "ultrasound scanner" or "scanner" or "ultrasound imaging device") refers to a wide variety of transducer types including but not limited to linear transducer, curved transducers, curvilinear transducers, convex transducers, microconvex transducers, and endocavity probes. In operation, an ultrasound scanner is often communicatively connected to a multi-purpose electronic device/display device to direct operations of the ultrasound scanner, optionally through one or more applications on the multi-purpose electronic device/display device (for example, via the Clarius™ App).

Figure 2:
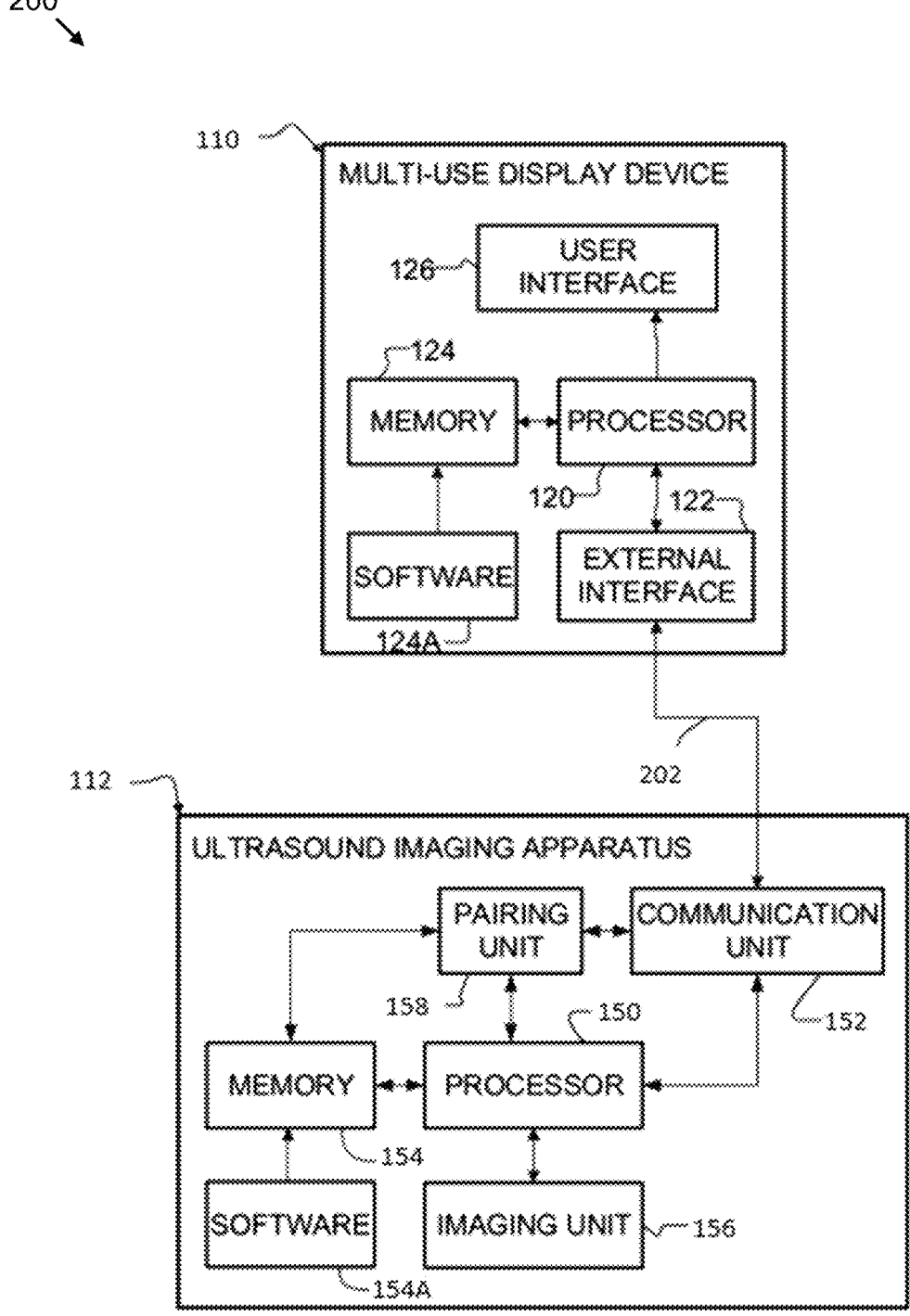
FIG. 2 is a schematic diagram of an ultrasound imaging system, according to an embodiment of the present invention.

The term "workflow application" or "application" (for example, via the Clarius™ App) or "workflow" refers to a software tool that assists with the automated activation and/or configuration of device feature(s). Conveyance to an operator may be visually on the display screen or via audio. This comprises activation and/or configuration of at least one regional setting on an ultrasound imaging device. In some embodiments of the invention, the workflow application guides the entire initiation and/or configuration processes automatically, optionally issuing screen display notifications to users/operators as needed, with triggers to complete tasks or with specific commands only if required. In some aspects of the present invention, a workflow application may be software 154A stored in memory 154 (FIG. 2). In some aspects of the invention, a workflow application on a mobile device conveys location data to a cloud-based server and, in response, receives from the cloud-based server one or more of: i) activation of at least one regional setting; 2) configuration of at least one regional setting; iii) activation of one or more licensed device features available for the ultrasound imaging device; all based on the location data and or periodically updated location data.

As used herein, the term "institution" may refer to a hospital, clinic, medical practice, or any other collection of users who may use an ultrasound scanner. In some embodiments, an "institution" may also have a single user. In some embodiments, institutions may be provided in a tiered or nested fashion. For example, an institution may have internal departments, divisions, or the like; and an ultrasound scanner may additionally or alternatively be associated with one or more such departments or divisions within an institution.

B. Exemplary Embodiments

In a first broad aspect of the present disclosure, there is provided a method for configuring at least one regional setting on an ultrasound imaging device comprising: the ultrasound imaging device receiving location data from a mobile device, via a connection therebetween; and the mobile device employing the location data, assigned to the ultrasound imaging device, to configure the at least one regional setting on the ultrasound imaging device.

In some embodiments, configuring the at least one regional setting enables the activation of one or more device features based on the location data assigned to the ultrasound imaging device, the method additionally comprises: identifying the one or more device features available for the ultrasound imaging device based on the location data; and activating the one or more device features at the ultrasound imaging device.

In some embodiments, the connection is a wireless communication connection established at the mobile device.

In some embodiments, the connection is a short-range wireless connection.

In some embodiments, the method further comprises: prior to identifying the one or more device features available for the ultrasound imaging device, verifying a current location assigned to the ultrasound imaging device against the location data received from the mobile device; and generating a location error when the current location does not match the location data from the mobile device, otherwise, proceeding to identify the one or more device features available for the ultrasound imaging device based on the current location.

In some embodiments, the method further comprises: following generation of the location error, updating the current location of the ultrasound imaging device with the location data received from the mobile device; and proceeding to identify the one or more device features available for the ultrasound imaging device based on the updated current location of the ultrasound imaging device.

In some embodiments, the method further comprises: determining, from the location data, an institution identifier associated with the mobile device; determining a geographic location using the institution identifier; and assigning the institution identifier as the location of the ultrasound imaging device.

In some embodiments, the method further comprises: prior to identifying the one or more device features available for the ultrasound imaging device, identifying one or more other devices associated with the institution identifier and determining one or more geographic locations associated with the one or more other devices; and generating a location error when at least one geographic location of the one or more locations is different, otherwise, proceeding to identify the one or more licensed features available for the ultrasound imaging device based on the location.

In some embodiments, the method further comprises: prior to identifying the one or more device features available for the ultrasound imaging device based on the location data, determining a geographic location from the location data; and determining, from the geographic location, that refined location data is required for identifying the one or more device features and proceeding to refine the location data with additional location data from a secondary source.

In some embodiments, the at least one regional setting comprises the one or more device features available for the ultrasound imaging device with a geographic location determined from the location data, the one or more device features being those approved by a regulatory authority for the geographic location.

In some embodiments, the location data is selected from the group consisting of a country code and Global Positioning System (GPS) co-ordinates.

In some embodiments, configuring the at least one regional setting enables activation of the ultrasound imaging device, the method additionally comprises: initiating an initial connection between the ultrasound imaging device and the mobile device; receiving, at the ultrasound imaging device, the location data from the mobile device via the initial connection; and establishing a communications connection at the ultrasound imaging device based on the location data.

In some embodiments, the initial connection is a short-range wireless connection which comprises one of a Bluetooth™ and a Zigbee™ connection.

In some embodiments, establishing an activation connection at the ultrasound imaging device based on the location data comprises: determining a geographic jurisdiction from the location data; determining a frequency band acceptable for the geographic location; and establishing the communication connection with the frequency band.

In some embodiments, establishing the communication connection at the ultrasound imaging device based on the location data comprises: updating a configuration of the communication connection with the location data associated with the initial connection.

In another broad aspect of the present disclosure, there is provided an ultrasound system for automatically configuring at least one regional setting on an ultrasound imaging device, the system comprising: the ultrasound imaging device; and a mobile device comprising a processor that is communicatively connected to the ultrasound imaging device and configured to: provide location data to the ultrasound imaging device; employ the location data, assigned to the ultrasound imaging device, to configure the at least one regional setting on an ultrasound imaging device.

In some embodiments, the processor is additionally configured to identify one or more device features available for the ultrasound imaging device based on the location data; and activate the one or more device features available for the ultrasound imaging device.

In some embodiments, the one or more device features available for the ultrasound imaging device based on the location data are those approved by a regulatory authority, within a geographic location determined by the location data.

In some embodiments, the mobile device is communicatively connected to the ultrasound imaging device by a wireless connection.

In some embodiments, the system additionally comprises a workflow application on the mobile device which provides the location data to a cloud-based server and, in response, receives from the cloud-based server an activation of one or more device features available for the ultrasound imaging device, based on the location data.

In another broad aspect of the present disclosure, there is provided a method for automatically activating one or more device features based on a location assigned to an ultrasound imaging device. The method comprises: upon initialization of the ultrasound imaging device, initiating a wireless connection between the ultrasound imaging device and a mobile device; identifying the one or more device features available for the ultrasound imaging device based on location data of the mobile device; and activating the one or more device features at the ultrasound imaging device.

In some embodiments, the method further comprises retrieving the location data associated with a wireless communication connection established at the mobile device.

In some embodiments, the method further comprises: prior to identifying the one or more device features available for the ultrasound imaging device, verifying a current location assigned to the ultrasound imaging device against the location data from the mobile device; and generating a location error when the current location does not match the location data from the mobile device, otherwise, proceeding to identify the one or more device features available for the ultrasound imaging device based on the current location.

In some embodiments, the method further comprises: following generation of the location error, updating the current location of the ultrasound imaging device with the location data received from the mobile device; and proceeding to identify the one or more device features available for the ultrasound imaging device based on the updated current location of the ultrasound imaging device.

In some embodiments, the method further comprises: prior to identifying the one or more device features available for the ultrasound imaging device, identifying one or more other devices associated with the institution identifier and determining one or more geographic locations associated with the one or more other devices; and generating a location error when at least one geographic location of the one or more locations is different, otherwise, proceeding to identify the one or more device features available for the ultrasound imaging device based on the location.

In some embodiments, the method further comprises: prior to identifying the one or more device features available for the ultrasound imaging device based on the location data, determining a geographic location from the location data; and determining, from the geographic location, that refined location data is required for identifying the one or more licensed features and proceeding to refine the location data with additional location data from a secondary source.

In another broad aspect of the present disclosure, there is provided an ultrasound system for automatically configuring automatically activating one or more device features based on a location assigned to an ultrasound imaging device. The system comprises: the ultrasound imaging device; and a mobile device comprising a processor that is communicatively connected to the ultrasound imaging device and configured to: upon initialization of the ultrasound imaging device, initiating a wireless connection between the ultrasound imaging device and the mobile device; identifying the one or more device features available for the ultrasound imaging device based on location data of the mobile device; and activating the one or more device features at the ultrasound imaging device.

In another broad aspect of the present disclosure, there is provided a method of automatically detecting a location of an ultrasound imaging device, the method comprises: retrieving location data associated with a first wireless communication connection established at a mobile device; initiating a short-range wireless connection between the ultrasound imaging device and the mobile device; and establishing a second wireless communication connection at the ultrasound imaging device based on a location data received from the mobile device via the short-range wireless connection.

In some embodiments, the method comprises: determining a geographic jurisdiction from the location data; determining a frequency band acceptable for the geographic location; and establish the second wireless communication connection with the frequency band. In some further embodiments, the method comprises: updating a configuration of the second wireless communication connection with the location data associated with the first wireless communication connection.

In another broad aspect of the present disclosure, there is provided an ultrasound system for automatically detecting a location of an ultrasound imaging device, the system comprises: the ultrasound imaging device; and a mobile device comprising a processor configured to: retrieve location data associated with a first wireless communication connection established at the mobile device; initiate a short-range wireless connection between the ultrasound imaging device and the mobile device; and establish a second wireless communication connection at the ultrasound imaging device based on the location data.

In another aspect of the present disclosure there is provided computer-readable media storing computer-readable instructions, which, when executed by a processor communicatively coupled with an ultrasound imaging device, cause the processor to provide location data to the ultrasound imaging device and to employ the location data, assigned to the ultrasound imaging device, to configure the at least one regional setting on an ultrasound imaging device.

In another aspect of the present disclosure there is provided a computer readable medium storing instruction for execution by a processor communicatively coupled with an ultrasound imaging device, within an ultrasound imaging system, wherein when the instructions are executed by the processor on a mobile device which, by configuring the at least one regional setting enables the activation of one or more licensed features based on a location assigned to the ultrasound imaging device, the processor additionally identifying the one or more licensed features available for the ultrasound imaging device based on the location data and activating the one or more licensed features at the ultrasound imaging device.

In another aspect of the present disclosure there is provided a computer readable medium storing instruction for execution by a processor communicatively coupled with an ultrasound imaging device, within an ultrasound imaging system, wherein when the instructions are executed by the processor on a mobile device, which by configuring at least one regional setting enables activation of the ultrasound imaging device, the processor additionally initiating an initial connection between the ultrasound imaging device and the mobile device; conveying to the ultrasound imaging device location data from the mobile device via the initial connection; and establishing a communications connection at the ultrasound imaging device based on the location data.

In another aspect of the present disclosure, there is provided a touchscreen device which is capable of communicating with an ultrasound imaging device, the touchscreen device includes: a processor; and a memory storing instructions for execution by the processor, wherein when the instructions are executed by the processor, the processor configures at least one regional setting which enables the activation of one or more licensed features based on a location assigned to the ultrasound imaging device, the processor additionally identifies the one or more licensed features available for the ultrasound imaging device based on the location data and activates the one or more licensed features which are available, at the ultrasound imaging device.

In another aspect of the present disclosure, there is provided a workflow tool for configuring at least one regional setting on an ultrasound imaging device. This workflow tool may be implemented through a processor within a multi-use device and/or mobile device communicatively associated with an ultrasound imaging device or through an application operated though a cloud-based server communicatively associated with one or both of an ultrasound imaging device and a multi-use device. A graphical user interface may be organized to convey to a user, for example a touchscreen, on a multi-use device communicatively associated with an ultrasound imaging device, one or more outcomes of an automatic and/or semi-automatic configuration and/or activation of the at least one regional setting. By way of example, an outcome may be notification of activation of one or more features, operational on the multi-use device (via the workflow tool), such features being approved for use based on configuration of the at least one regional setting on an ultrasound imaging device.

In another broad aspect of the present disclosure, there is provided a server comprising at least one processor and at least one memory storing instructions for execution by the at least one processor, wherein when executed, the instructions cause the at least one processor to receive a location assigned to an ultrasound imaging device by a multi-use device and/or mobile device communicatively connected thereto, and thereafter to configure the at least one regional setting on an ultrasound imaging device.

The system and method of the present invention enables location-based activation and/or configuration of an ultrasound imaging device, via communication with and direction from a mobile device. In one aspect, location-based configuration enables activation of features which are operationally and/or legally permitted within that location, for example features which are approved for use by a governmental agency and/or regulatory body and/or certification body within the bounds of a location.

There are increasing commercial advantages in portable, handheld (sometimes wireless) ultrasound imaging devices, often referred to as POCUS (point of care ultrasound) devices, which are often the size of a smartphone. Such devices do not have built in interface screens and reply upon connections to multi-use devices/mobile devices for set-up and scanning control. The method and system of the invention provides an activator tool which is particularly useful in the activation and configuration of POCUS devices. Such an imaging device uses a transducer (e.g., a piezoelectric or capacitive device operable to convert between acoustic and electrical energy) to scan a planar region or a volume of an anatomical feature. Electrical and/or mechanical steering allows transmission and reception along different scan lines wherein any scan pattern may be used. Ultrasound data representing a plane or volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data is data which represents an anatomical feature sought to be assessed and reviewed by a sonographer.

FIG. 1 is a schematic diagram of a system 100 with multiple ultrasound imaging devices 112 in accordance with an embodiment of the disclosure. In the system 100 shown, there are multiple ultrasound imaging devices 112 connected to their corresponding mobile devices 110 and either connected directly, or indirectly via the mobile devices 110, to a communications network 140, such as the internet. One or more of the ultrasound imaging devices 112 and mobile devices 110 shown in FIG. 1 may be the same or different as the other.

Mobile devices 110 are often more versatile than ultrasound imaging devices 112 and can supplement and enable the functionalities offered by the ultrasound imaging devices 112. As will be described herein, the device settings and/or a workflow application at the mobile device 110 can be leveraged to adapt the configuration of the ultrasound imaging devices 112, which can increase security and reliability of the overall system 100. For example, ultrasound imaging devices 112, when sold, are often configured by default to North American wireless communication settings (e.g., channel 165 on the 5 GHz network). This setting will apply for a majority of the world but, for some countries, this default setting will not work. As a result, in those countries, after initialization, the ultrasound imaging device 112 will not automatically communicate with the mobile device 110 and instead, requires manual changes to its device settings, including wireless communication settings. With the disclosed embodiments, the location data from the mobile device 110 can be leveraged to configure the regional setting(s) at the ultrasound imaging device so that, upon initialization, there is a seamless connection with the necessary devices (including the mobile device 110) as well as availability of the appropriate functionalities.

Generally, the ultrasound imaging devices 112 may have any of a wide range of various sizes and configurations. For example, the ultrasound imaging device 112 may be handheld or hand carried. Alternatively, the ultrasound imaging device 112 may be in a laptop form factor or a more traditional cart-based device. In some preferred embodiments, the ultrasound imaging device 112 may have the form of hand-held battery-powered probes.

The ultrasound imaging devices 112 may be connected via the communications network 140 to a server 130. The server 130 may include a processor, which may be connected to a non-transitory computer readable memory storing computer readable instructions, which, when executed by the processor, cause the server to provide one or more of the functions of the system 100. The server 130 may be a cloud-based server configured to communicate with the mobile devices 110 via a workflow application installed thereon, or in another fashion. The ultrasound imaging devices 112 may be connected to the mobile devices 110 via link 102 which is described further below as link 202.

Figure 11:
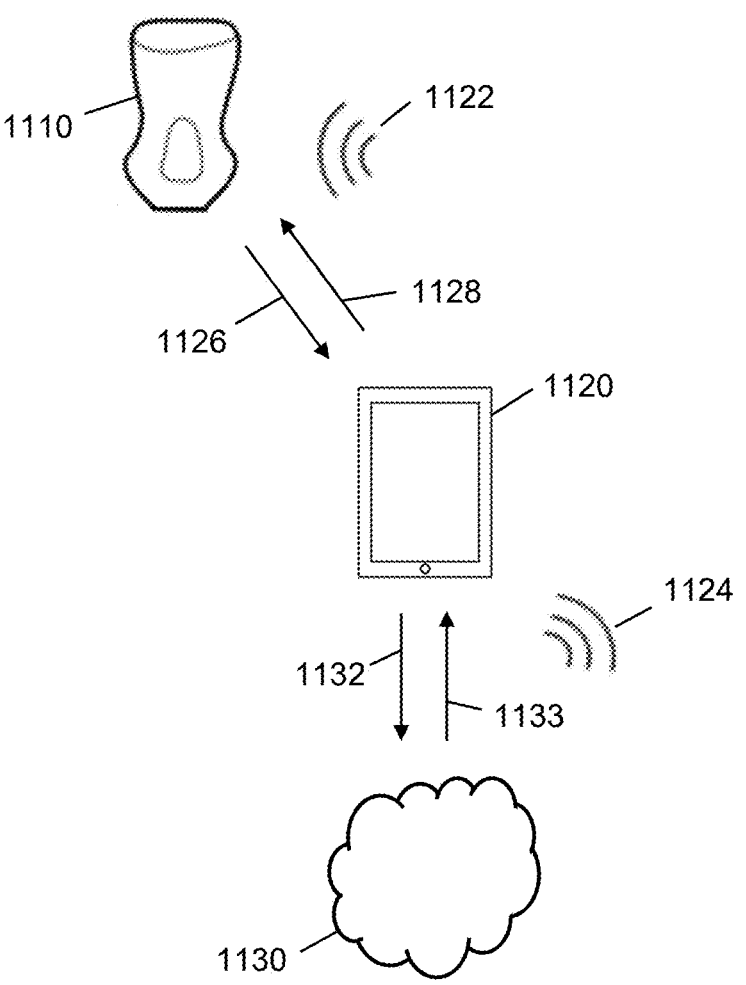
FIG. 11 is schematic diagram of the broad architecture of the system of the present invention.

A further embodiment of the system of the invention is further exemplified in FIG. 11, which provides a schematic diagram of a system 1100 with ultrasound imaging device 1110. In the system 1100 shown, ultrasound imaging device 1110 is connected to mobile device 1120 either connected directly, or indirectly via the mobile devices 1120, to a communications network 1122, such as the internet. Signals 1126 and 1128 are conveyed via this communications network 1122. server 130. Mobile device 1120 is communicably connected by communications network 1124 to server 1130 (which itself may include a processor, which may be connected to a non-transitory computer readable memory storing computer readable instructions, which, when executed by the processor, cause the server to provide one or more of the functions of the system 1100). Signals 1132 and 1133 are conveyed via this communications network 1124. The server 1130 may be a cloud-based server configured to communicate with mobile devices 1110 via a workflow application installed thereon, or in another fashion.

FIG. 2 is a schematic diagram of an example system 200 composed of an example mobile device 110 in communication with an example ultrasound imaging device 112.

The ultrasound imaging device 112 may be wirelessly connected with the mobile device 110. The ultrasound imaging device 112 may transmit an ultrasound signal to a target object according to a control signal that is transmitted from the mobile device 110. A communication link 202 between the mobile device 110 and the ultrasound imaging device 112 may be established. The mobile device 110 may gather information about the ultrasound imaging device 112 by way of link 202. The mobile device 110 may establish communication link 202 with one or more other ultrasound imaging devices 112 and may obtain and use information about the ultrasound imaging devices 112 for other purposes.

The mobile device 110 may comprise a processor 120, memory 124, user interface 126, and an external interface 122. The processor 120 may be a general-purpose central processing unit (CPU) or may be a low power/mobile specific processor. The processor 120 is coupled with the memory 124. The memory 124 includes storage for program and program operating code. One or more programs 124A in memory 124 coordinates interactions of the mobile device 110 with ultrasound imaging devices 104 as described herein.

The user interface 126 is coupled with processor 120 and may comprise both the software and hardware components necessary to interface with a user of the mobile device 110. The user interface 126 may comprise physical input devices such as a touch sensitive display screen, keyboard, microphone, or function buttons. The user interface 126 may further comprise output devices such as a color, grayscale, or black and white display screen, audio speaker/output, vibrating or LED indicators.

The external interface 122 is coupled with the processor 120 and provides connectivity of the mobile device 110 with the ultrasound imaging device(s) 112 though communication link(s) 202. The external interface 122 may also be operable to communicate with another device, such as a web server.

The processor 120 may generate control signals to control an operation of ultrasound imaging device 112 according to information that is provided via the user interface 126. The control signals may include control signals that control ultrasound imaging device 112 to generate ultrasound signals, and control signals that control how ultrasound imaging device 112 handles transmission and reception of the ultrasound signal. In addition, the processor 120 may control wireless communication with the ultrasound imaging device 112; and may control generation and display of an ultrasound image on a display of user interface 126 based on ultrasound image data provided from ultrasound imaging device 112.

The ultrasound imaging device 112 may comprise a processor 150, memory 154 (storing software 154A), imaging unit 156, pairing unit 158, and a communication unit 152. The processor 150 may comprise a general-purpose CPU, a low power/mobile specific processor, a field programmable gate array (FPGA), a combination of two or more of these or the like.

The imaging unit 156 is operable to acquire ultrasound image data of a target object based on control signals from processor 150. The imaging unit 156 may comprise a transmitter for generating ultrasound energy and a receiver for receiving ultrasound energy reflected from the target object. The imaging unit 156 may further comprise an analog-to-digital converter for digitizing the received ultrasound energy into digital ultrasound data. The imaging unit 156 may further comprise one or more beamformers to combine and focus the received ultrasound energy along a desired scanline. The imaging unit 156 may further comprise a signal processor to apply filtering or compression to the ultrasound image data. The imaging unit 156 may also comprise a scan converter for converting the ultrasound image data into a specific display format.

The processor 150 is coupled with memory 154. The memory 154 includes storage for program and program operating code. One or more programs in memory 154 coordinates the operation of the ultrasound imaging device 112 as described herein. The memory 154 may also be used to store information about ultrasound imaging device 112 and/or ultrasound image data. The memory 154 can include a non-transitory computer readable memory for storing computer readable instructions, which, when executed by the processor 150, may cause the ultrasound imaging device 112 to provide one or more of the functions of the system 200. Such functions may be, for example, the acquisition of ultrasound data, the processing of ultrasound data, the scan conversion of ultrasound data, the transmission of ultrasound data or ultrasound frames to a display device, the detection of operator inputs to the ultrasound scanner, and/or the switching of the settings of the ultrasound scanner.

The pairing unit 158 is operable to establish the communication link 202 between the communication unit 152 and the external interface 122 of the mobile device 110. The communication unit 152 may comprise one or more wireless transceivers.

The communication link 202 may comprise more than one communication protocol. The protocol used for communications between the ultrasound imaging device 112 and the mobile device 110 may be WiFi™, Bluetooth™ or Zigbee™, for example, or any other suitable two-way radio communications protocol. In some embodiments, the ultrasound imaging device 112 may operate as a WiFi™ hotspot, for example. In some embodiments, the communication link 202 may be wired. For example, the ultrasound imaging device 112 may be attached to a cord that may be pluggable into a physical port of the the mobile device 110.

In some embodiments, a first protocol is applied for initial discovery or initialization of the ultrasound imaging device 112 by the mobile device 110. An initial connection can be established with the first protocol. For example, via the first protocol, information useful for establishing a communications connection according to a second protocol with the ultrasound imaging device 112 may be obtained. The second protocol may provide a longer range and/or higher bandwidth connection than the first protocol. For example, the first protocol may be a Bluetooth™ low energy (BLE) connection and the second protocol may be a Wi-Fi connection. Alternatively, one or more of the following protocols may be used: wireless local area network (LAN), Bluetooth, ZigBee™, Wi-Fi Direct (WFD), ultra wideband (UWB), infrared data association (IrDA), Bluetooth low energy (BLE), near field communication (NFC), wireless broadband internet (Wibro), world interoperability for microwave access (WiMAX), shared wireless access protocol (SWAP), radio frequency (RF) communications and the like.

In some embodiments, the ultrasound imaging devices 112 can advertise their presence. For example, the communication unit 152 may include a Bluetooth Low Energy module that is configured to periodically advertise the presence of the ultrasound imaging device 112. Upon reception of one of these advertisements, the mobile device 110 may attempt to establish the initial connection with the ultrasound imaging device 112 to obtain information for establishing another communication link. For example, the communication link 202 between the mobile device 110 and the ultrasound imaging device 112 can be implemented by the initial connection. Via this initial connection, the mobile device 110 can push a regional setting to the ultrasound imaging device 112. The mobile device 110 can receive aspects of the regional setting from a workflow application installed thereon that is in communication with the cloud-based server 130 in some embodiments. The mobile device 110 can employ its location data to trigger the cloud-based server 130 to automatically identify various regional settings for the ultrasound imaging device 112, such as but not limited to, a communication domain and wireless channel configuration. Other regional settings that may vary with the location data, such as language, time zone, and/or local preferences, may be configured at the ultrasound imaging device 112.

The mobile device 110 can also trigger the cloud-based server 130 to determine the device features that can be activated based on the location data. Device features of the ultrasound imaging device 112 are typically deactivated at sale. Device features may not be approved for use in all jurisdictions due to regulatory constraints or may be restricted by license terms. The regional setting can include one or more device features available for the ultrasound imaging device 112 within a geographic location determined from the location data. Those device features are those approved by a regulatory authority for the geographic location. For example, certain artificial intelligence (AI)-based features, such as identifying and verifying musculoskeletal features/regions of interest (e.g., bladder volume), optimal imaging of muscles and tissues, and automatically predicting fetal biometric measurements on an ultrasound image, may not be approved by all regulatory authorities around the world. When the ultrasound imaging device 112 is configured with the methods and systems described herein, it can be seamlessly configured by the location data of the mobile device 110 so that the appropriate regional settings, including device features, are configured after initialization of the ultrasound imaging device 112.

Within the scope of the present invention, a lookup table or database that comprises regulations for different locations may be used for identifying the regulations for the current location of the ultrasound imaging device. The lookup table may be stored in server/cloud 1130 and retrieved by mobile device 1120 over a network (such as shown as 1124 in FIG. 11). Lookup table may be updated and changed in accordance with changing laws in each region, area, state, province, country, jurisdiction etc. . . . (however defined). The identified regulations may be used, as described herein to modify certain operating parameters that are available to the ultrasound imaging device in order to comply with regulations. The mobile device is enabled to identify regulations via cloud/server access to the lookup table or database that includes regulations for different locations (or at least regulation associated with one given location). By way of example, a device feature for an ultrasound imaging device may include artificial intelligence models and/or presets which require regulatory approval prior deployment and use in connection with an ultrasound imaging device (without limitation, such as bladder AI models, musculoskeletal AI models, obstetric AI models)

Figure 3:
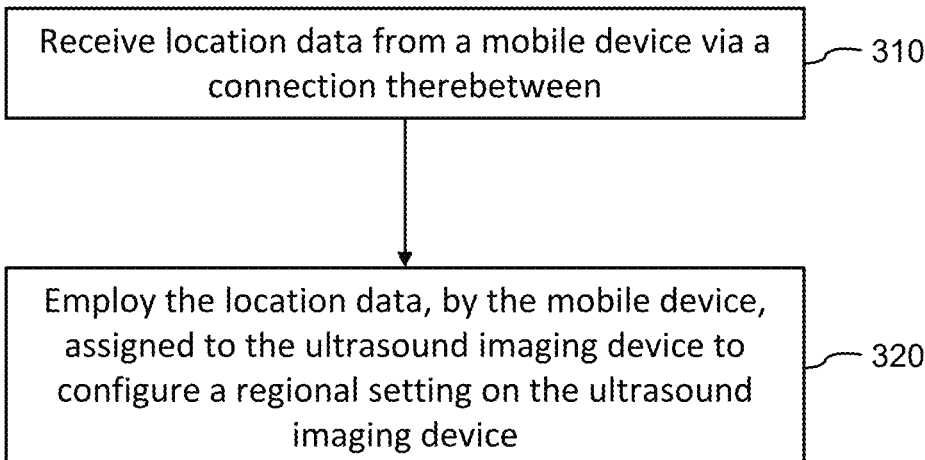
FIG. 3 is a flowchart diagram showing steps of a method for configuring at least one regional setting on an ultrasound imaging device, in accordance with at least one embodiment of the present invention.
Figure 4A:
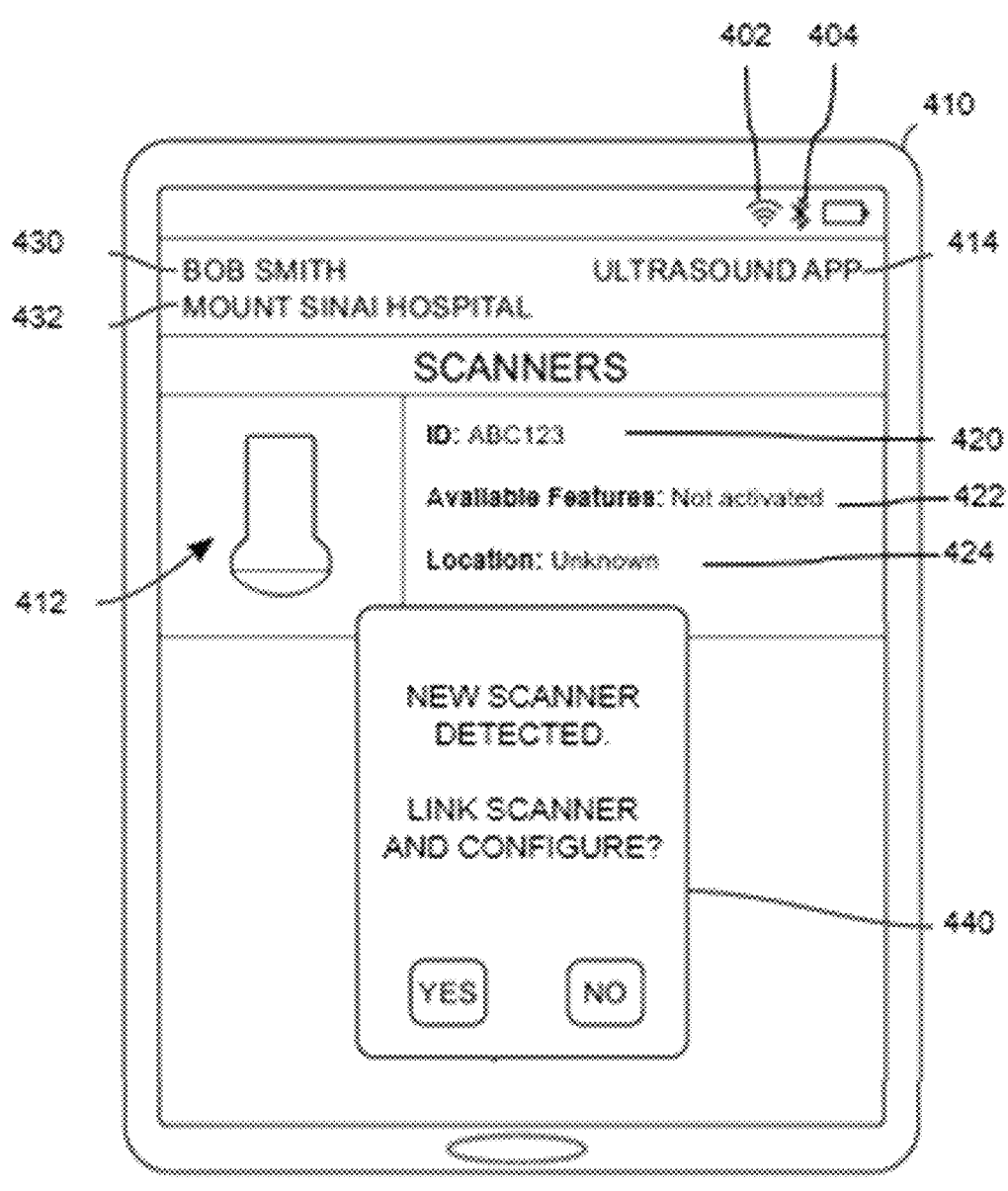
FIG. 4A is an example screenshot of a user interface at a mobile device, in accordance with at least one embodiment of the present invention.
Figure 4B:
FIG. 4B is another example screenshot of the user interface of FIG. 4A, in accordance with at least one embodiment of the present invention.

Reference will now be made to FIG. 3, which is a flowchart diagram of a method 300 provided in accordance with one embodiment of the invention for configuring at least one regional setting on the ultrasound imaging device 112. Reference will also be made to FIGS. 4A and 4B which are example screenshots 400A and 400B of a user interface at a mobile device 410.

At step 310, the ultrasound imaging device 112 receives location data from the mobile device 110 via a connection therebetween.

The connection between the mobile device 110 and the ultrasound imaging device 112 can include a wired connection and/or a wireless communication connection, such as but not limited to, a short-range wireless connection. The short-range wireless connection can include a Bluetooth™ or Zigbee™ connection.

The location data relates to a geographic location of the mobile device 110. The location data can include data related to a range of granularity levels, such as a country, a region composed of several countries (e.g., continent) or within a country (e.g., city, state/province, or area composed of several cities or townships), and/or an institution. The location data can be selected from the group consisting of a country code and Global Positioning System (GPS) coordinates.

Generally, the location data is sufficient to relate to a regulatory regime to enable identification of any constraints on the regional settings that can be configured at the ultrasound imaging device 112. In many cases, a country code is sufficient information as most regulatory legal regime operates at a federal or country wide level (e.g., USA and Canada). In another example, the country code may be unnecessary. For example, for the European Union, there is one regulatory body and so, the location data needs to be sufficient only to trigger the corresponding regional regulatory body. In some jurisdictions, regulatory regimes may be broken down more regionally, as opposed to nationally, and so, the country code may not be sufficient for defining the regional setting in some cases. It may be that more refined regional location data is required. In those cases, the mobile device 110 can proceed to refine the location data with additional location data from one or more secondary sources, such as GPS, user inputs, the cloud-based server 130, nearby access points and/or a third-party geolocator.

FIG. 4A is an example screenshot 400A of a user interface of an example workflow application 414 ("Ultrasound App") at the mobile device 410. The workflow application 414 is associated with a user identifier 430 ("Bob Smith") and an institution identifier 432 ("Mount Sinai Hospital"). As can be seen, the ultrasound imaging device 412, identified with identifier 420 "ABC123", is detected via an initial connection 404, which is based on Bluetooth™ in this example. The mobile device 410 is connected to a wireless connection 402 as well. In this example, the ultrasound imaging device 412 has not yet been initialized and so, the available features list 422 is not available and the location identifier 424 is unknown. Upon connection between the mobile device 410 and the ultrasound imaging device 412, an example configuration interface 440 such as shown in FIG. 4A can appear inquiring whether the ultrasound imaging device 412 can be linked with the mobile device 410 and also configured by the mobile device 410.

In some embodiments, the mobile device 110 can be configured to determine, from the location data, an institution identifier to assign to the ultrasound imaging device 112. Referring to FIG. 4A, the mobile device 110 is associated with the institution identifier 432 ("Mount Sinai Hospital"). The location data assigned to the ultrasound imaging device 112 can include the institution identifier 432. The mobile device 110 can be configured to determine a geographic location using the institution identifier 432.

The mobile device 110 can, in some embodiments, be configured to identify other devices associated with the institution identifier 432 to verify the geographic locations of those devices. In the case that the mobile device 110 determines that there are inconsistencies between the geographic locations assigned to any of those devices, the mobile device 110 can generate a location error.

At step 320, the mobile device 110 employs the location data assigned to the ultrasound imaging device 112 to configure the at least one regional setting on the ultrasound imaging device 112.

In some embodiments, to determine the regional settings to be configured at the ultrasound imaging device 112, the mobile device 110 can engage with the cloud-based server 130 via the workflow application 414 to determine the regional settings that is appropriate, or approved, for the ultrasound imaging device 112 based on the location data. The workflow application 414 can provide the location data to the cloud-based server 130, and receive data related to the regional settings, such as activation of device features for the ultrasound imaging device 112 based on the location data.

The regional settings can vary with the location data as regulatory restrictions may not allow all device features to be used or may require specific settings, and there can be limitations on device features that are under license terms. By automatically configuring the ultrasound imaging device 112 based on the location data from the mobile device 110, the regional setting at the ultrasound imaging device 112 can be activated seamlessly and accurately.

For example, the cloud-based server 130 can identify one or more device features that are available for the ultrasound imaging device 112 based on the location data and advise the mobile device 110 via the workflow application 414 accordingly. Referring now to FIG. 4B, the ultrasound imaging device 412 is now linked to the mobile device 410. As can be seen, the location identifier 424' is updated to "Canada", which was determined from the location data provide by the mobile device 110. The regional settings configured by the mobile device 110 includes activating features "AI+" and "OB AI" now in the updated features list 422', which were determined to be features available for the location updated in the location identifier 424'. The mobile device 110 can then configure the regional settings for the ultrasound imaging device 112 based on the device feature(s) identified by the cloud-based server 130. The configuration of the regional settings can involve activating those device features, such as those in the features list 422', at the ultrasound imaging device 412.

The regional setting configured at the ultrasound imaging device 112 can include establishing a communications connection based on the location data, such as parameters for a wireless communication connection to be configured at the ultrasound imaging device 112. The mobile device 110 can be configured to determine a frequency band acceptable for the geographic location determined from the location data and proceed to configure the regional setting at the ultrasound imaging device 112 to establish the wireless communication connection with that frequency band. In some embodiments, the mobile device 110 can configure the ultrasound imaging device 112 to update an existing configuration of the communication connection.

Prior to determining the regional settings, the mobile device 110 can be configured to verify a current location assigned to the ultrasound imaging device 112 against the location data received from the mobile device 110. This can be a routine verification step or can be triggered when the ultrasound imaging device 112 is already assigned a current location, which may be the case when a default location setting is assigned or the ultrasound imaging device 112 may have previously been initialized and now moved to another location for use. In the case that the mobile device 110 determines that the current location matches the location data, the mobile device 110 can then proceed to identify the regional settings for the ultrasound imaging device 112, such as the device features available based on the current location.

Should the current location not match the location data from the mobile device 110, the mobile device 110 can be configured to generate a location error. The mobile device 110 can proceed to update the current location of the ultrasound imaging device 112 with the location data received from the mobile device 110. The mobile device 110 can then proceed to identify the regional settings for the ultrasound imaging device 112 based on the updated current location.

Figure 5:
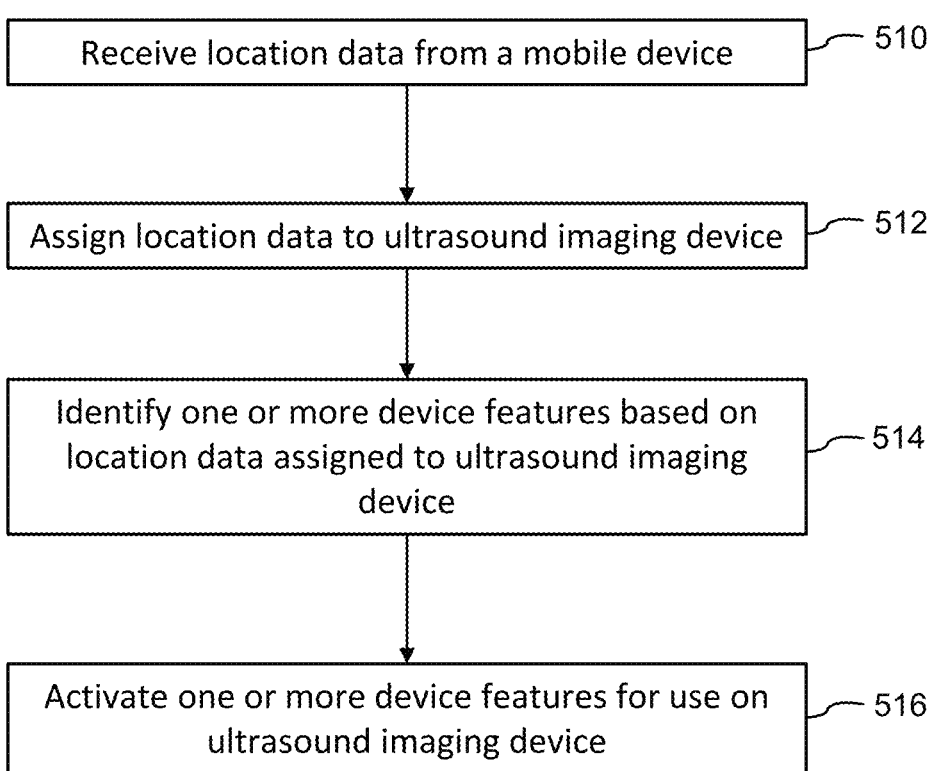
FIG. 5 is a flowchart diagram showing steps of a method for identifying one or more device features, in accordance with at least one embodiment of the present invention.

Reference will now be made to FIG. 5, which is a flowchart diagram of a method 500 provided in accordance with one embodiment of the invention for configuring at least one regional setting on the ultrasound imaging device 112. At step 510, the ultrasound imaging device 112 receives location data from the mobile device 110 via a connection therebetween. As noted above, the connection between the mobile device 110 and the ultrasound imaging device 112 can include a wired connection and/or a wireless communication connection, such as but not limited to, a short-range wireless connection. The short-range wireless connection can include a Bluetooth™ or Zigbee™ connection. The location data relates to a geographic location of the mobile device 110. In this manner, and at step 512, an ultrasound imaging device is "assigned" location data. At step 514, based upon the location data, which was assigned to ultrasound imaging device, one or more device features are identified which would be available to for activation and then use on the ultrasound imaging device. These device features which are available are then activated at steps 516, for use in scanning on the ultrasound device and processing on the multi-use display device communicably connected to the ultrasound scanner.

Reference will now be made to FIG. 6, which is a flowchart diagram of a method 600 provided in accordance with one embodiment of the invention for verifying a location of an ultrasound imaging device 112. At step 610, mobile device 110 receives location data from ultrasound imaging device 112. As noted above, the connection between the mobile device 110 and the ultrasound imaging device 112 can include a wired connection and/or a wireless communication connection, such as but not limited to, a short-range wireless connection. The short-range wireless connection can include a Bluetooth™ or Zigbee™ connection. At step 612, the mobile device verifies or cross-checks the location of the ultrasound imaging device (received from step 610) to a location of the mobile device to determine if such locations "match". If there is a match or correlation of locations, at step 614, one or more device features are made available to the ultrasound imaging device, based upon the location of the mobile device/ultrasound imaging device "match". If there is no match, at step 616, an allocation error is generated. This error may trigger step 618, which is the updating of location of the ultrasound imaging device to correct the location data, from the mobile device. Such correction being applied, one or more device features are made available to the ultrasound imaging device, based upon the location of the mobile device/ultrasound imaging device "match".

Reference will now be made to FIG. 7, which is a flowchart diagram of a method 700 provided in accordance with one embodiment of the invention for initiating a connection between ultrasound imaging device 112 and a mobile device 110. At step 710, an initial connection is commenced or initiated between ultrasound imaging device 112 and mobile device 110. At step 712, location data is received at ultrasound imaging device 112, from mobile device 110 through the initial connection. It is preferred in many instances, although not required, that this initial connection is facilitated through a short-wave connection. This step may serve to determine a frequency band acceptable for the location. At step 714, a communications connection is established using the frequency band, previously determined, and based upon the location data. It is preferred in many instances, although not required, that this communications connection is facilitated through one or more the following; wireless (e.g. 2G, 3G, 4G, 5G, WiFi®, WiMAX®, Wireless USB (Universal Serial Bus), Zigbee®, Bluetooth® and satellite), and/or hard wired connections such as local, internet, ADSL (Asymmetrical Digital Subscriber Line), DSL (Digital Subscriber Line), cable modem, T1, T3, fiber-optic, dial-up modem.

Reference will now be made to FIG. 8, which is a flowchart diagram of a method 800 provided in accordance with one embodiment of the invention for monitoring ultrasound imaging device, such as 1110 in FIG. 11. At step 810, location data of the ultrasound imaging device 1110 is monitored, by mobile device 1120 via a connection therebetween. This monitoring may be ongoing or intermittent so as to ensure that the features deployed and used on the ultrasound imaging device are jurisdictionally and/or geographically approved (for example legally permitted under a regulatory regime). The location data relates to a geographic location of the mobile device 1110. At step 820, mobile device 1120 enables a cross-check or verification of the device features which had been deployed and previously approved on ultrasound imaging device 1110 to determine if those features are still approved based on the location data. At step 830, wherein there is a match between location data and device features, activation of such features is maintained and permitted. At step 840, wherein there is a disparity in location data (lack of matching), one or more features are deactivated in order to comply, for example with a regulatory regime or set of rules.

Figure 9:
FIG. 9 is a flowchart diagram showing steps of a method for activating features in whole or part, deactivating features and monitoring location in accordance with at least one embodiment of the present invention.

Reference will now be made to FIG. 9, which is a flowchart diagram of a method 900 provided in accordance with one embodiment of the invention for activating device features in whole or part, declining features and monitoring location verifying a location of an ultrasound imaging device, such as 1110 in FIG. 11. As described herein, mobile device 1120 receives location data from ultrasound imaging device 1110 via a connection therebetween and thereafter ultrasound imaging device configures the regional settings of the ultrasound imaging device via the conveyed location data. At step 920, one of more device features are identified, such as those which may be made available to the ultrasound imaging device based on location data. Subsequent options, thereafter, include steps 930, 940 and 950. Device features are activated in whole at step 930, based upon jurisdiction and/or geography. Device features are activated in part at step 940, based upon jurisdiction and/or geography. Activation of device features is declined at step 950, based upon jurisdiction and/or geography. Wherein there is activation of device features in whole or part, ongoing location monitoring may be applied at steps 960.

Figure 10:
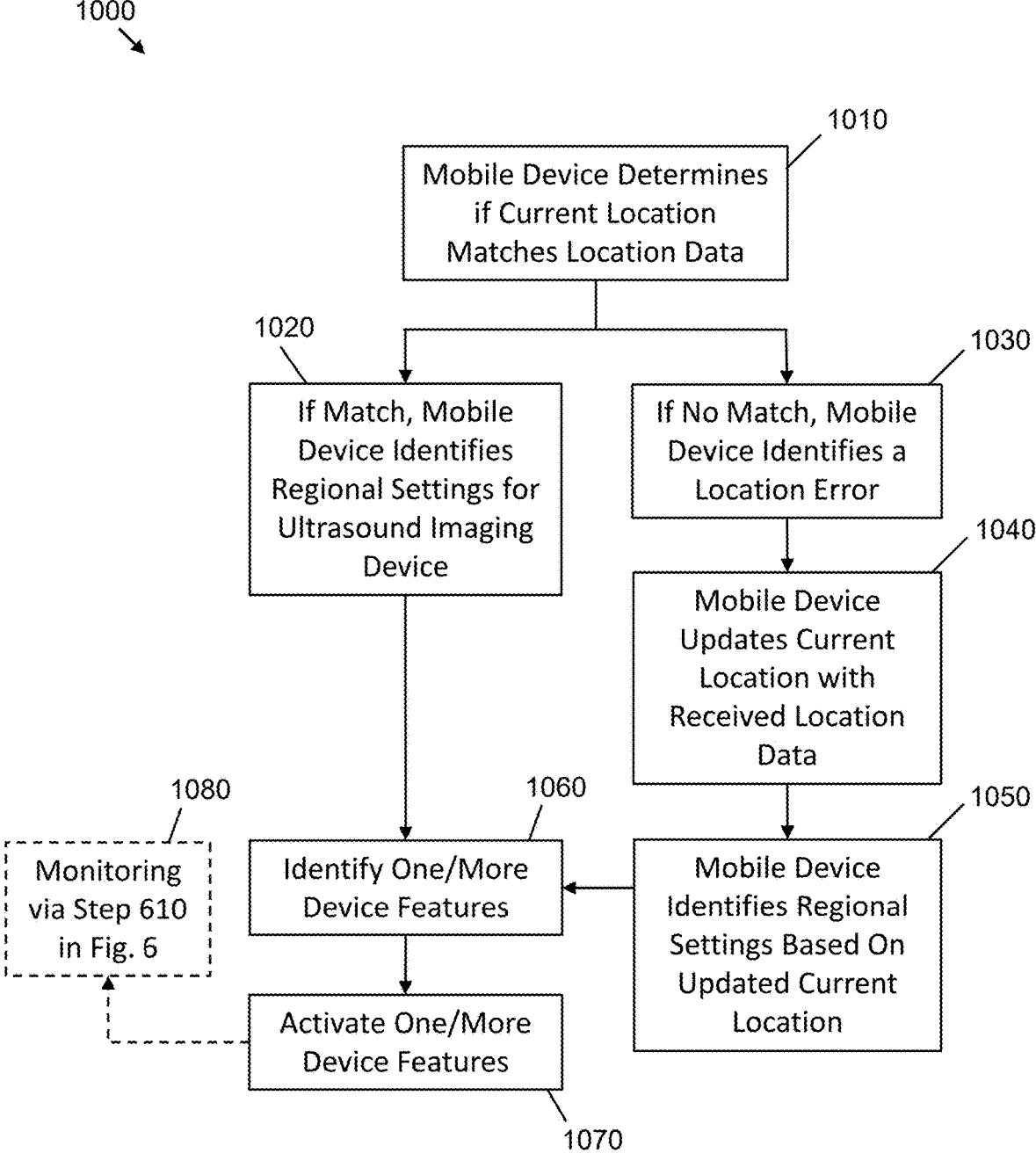
FIG. 10 is a flowchart diagram showing steps of a method for change location protocols, in accordance with at least one embodiment of the present invention.

Reference will now be made to FIG. 10, which is a flowchart diagram of a method 1000 provided in accordance with one embodiment of the invention diagram showing steps for location protocol options. Mobile device, such as 1120 in FIG. 11 determines at step 1010 if current location of the ultrasound imaging device 1110 matches location data (as ascertained by the methods described herein). There are then two options: at step 1020 if there is determined to be a match, the mobile device identified regional settings for ultrasound imaging device and at step 1030, with not match a location error is generated. From step 1020, one ore more device features are identified at step 1060, available features are activated at step 1070 and optional ongoing location monitoring occurs at step 1080. From step 1030, mobile device may update current location with received location data such that, at steps 1050, mobile device may then identify regional settings based on updated current location. From step 1050, one or more device features are identified at step 1060, available features are activated at step 1070 and optional ongoing location monitoring occurs at step 1080.

For simplicity and clarity of illustration, where considered appropriate, reference numerals may be repeated among the figures to indicate corresponding or analogous elements or steps. In addition, numerous specific details are set forth in order to provide a thorough understanding of the exemplary embodiments described herein. However, it will be understood by those of ordinary skill in the art that the embodiments described herein may be practiced without these specific details. In other instances, certain steps, signals, protocols, software, hardware, networking infrastructure, circuits, structures, techniques, well-known methods, procedures and components have not been described or shown in detail in order not to obscure the embodiments generally described herein.

Furthermore, this description is not to be considered as limiting the scope of the embodiments described herein in any way. It should be understood that the detailed description, while indicating specific embodiments, are given by way of illustration only, since various changes and modifications within the scope of the disclosure will become apparent to those skilled in the art from this detailed description. Accordingly, the specification and drawings are to be regarded in an illustrative, rather than a restrictive, sense.

The system of the present invention uses a transducer (e.g., a piezoelectric or capacitive device operable to convert between acoustic and electrical energy) to scan a planar region or a volume of an anatomical feature. Electrical and/or mechanical steering allows transmission and reception along different scan lines wherein any scan pattern may be used. Ultrasound data representing a plane or volume is provided in response to the scanning. The ultrasound data is beamformed, detected, and/or scan converted. The ultrasound data may be in any format, such as polar coordinate, Cartesian coordinate, a three-dimensional grid, two-dimensional planes in Cartesian coordinate with polar coordinate spacing between planes, or other format. The ultrasound data is data which represents an anatomical feature sought to be assessed and reviewed by a sonographer.

In various embodiments, a multi-purpose electronic devices/display devices may be, for example, a laptop computer, a tablet computer, a desktop computer, a smart phone, a smart watch, spectacles with a built-in display, a television, a bespoke display or any other display device that is capable of being communicably connected to an ultrasound imaging device/probe. Multi-purpose electronic devices/display devices may host a screen (such as shown in FIGS. 1 and 2), and may include a processor, which may be connected to a non-transitory computer readable memory storing computer readable instructions, which, when executed by the processor, cause the display device to provide one or more of the functions of the system (such system comprising at least one multi-purpose electronic device and at least probe). Such functions may be, for example, the receiving of ultrasound data that may or may not be pre-processed; scan conversion of received ultrasound data into an ultrasound image; processing of ultrasound data in image data frames; the display of a user interface; the control of a probe and the display of an ultrasound image on the screen. Such a screen may comprise a touch-sensitive display (e.g., touchscreen) that can detect a presence of a touch from the operator on screen and can also identify a location of the touch in screen. The touch may be applied by, for example, at least one of an individual's hand, glove, stylus, or the like. As such, the touch-sensitive display may be used to receive an input, for example, indicating the presence or absence of text or annotations on an image. The screen and/or any other user interface may also communicate audibly. Multi-purpose electronic devices/display devices may be configured to present information to the operator during or after the imaging or data acquiring session. The information presented may include ultrasound images (e.g., one or more 2D frames), graphical elements, measurement graphics of the displayed images, user-selectable elements, user settings, and other information (e.g., administrative information, personal information of the patient, and the like).

Also stored in the computer readable memory within the multi-purpose electronic devices/display devices may be computer readable data which may be used by processors within multi-purpose electronic devices/display devices, in conjunction with the computer readable instructions within multi-purpose electronic devices/display devices, to provide the functions of the system. Such computer readable data may include, for example, settings for ultrasound probe, such as presets for acquiring ultrasound data and settings for a user interface displayed on screens. Settings may also include any other data that is specific to the way that the ultrasound probe operates or that multi-purpose electronic devices/display devices operate.

D. Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

the singular forms "a", "an", and "the" also include the meaning of any appropriate plural forms.

Unless the context clearly requires otherwise, throughout the description and the claims:

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

Embodiments of the invention may be implemented using specifically designed hardware, configurable hardware, programmable data processors configured by the provision of software (which may optionally comprise "firmware") capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs"), and the like. Examples of configurable hardware are: one or more programmable logic devices such as programmable array logic ("PALs"), programmable logic arrays ("PLAs"), and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

For example, while processes or blocks are presented in a given order herein, alternative examples may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed in parallel or may be performed at different times.

The invention may also be provided in the form of a program product. The program product may comprise any non-transitory medium which carries a set of computer-readable instructions which, when executed by a data processor (e.g., in a controller and/or ultrasound processor in an ultrasound machine), cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or pre-programmed chips (e.g., EEPROM semiconductor chips), nanotechnology memory, or the like. The computer-readable signals on the program product may optionally be compressed or encrypted.

Where a component (e.g. a software module, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples but should be given the broadest interpretation consistent with the description as a whole.

The invention claimed is:

1. A method for configuring at least one regional setting on an ultrasound scanner, the method comprising:
    the ultrasound scanner forming a connection with a mobile display device, wherein the mobile display device is for displaying ultrasound images acquired by the ultrasound scanner;
    the mobile display device determining its location data and assigning the location data to the ultrasound scanner; and
    configuring the at least one regional setting on the ultrasound scanner based on the location data of the mobile display device assigned to the ultrasound scanner.

2. The method of claim 1, wherein configuring the at least one regional setting enables the activation of one or more device features based on the location data assigned to the ultrasound scanner, the method additionally comprises:
    identifying the one or more device features available for the ultrasound scanner based on the location data; and
    activating the one or more device features at the ultrasound scanner.

3. The method of claim 2 further comprises:
    prior to identifying the one or more device features available for the ultrasound scanner, verifying a current location assigned to the ultrasound scanner against the location data received from the mobile display device; and
    generating a location error when the current location does not match the location data from the mobile display device, otherwise, proceeding to identify the one or more device features available for the ultrasound scanner based on the current location.

4. The method of claim 3 further comprises:
    following generation of the location error, updating the current location of the ultrasound scanner with the location data received from the mobile display device; and
    proceeding to identify the one or more device features available for the ultrasound scanner based on the updated current location of the ultrasound scanner.

5. The method of claim 2 further comprises:
    determining, from the location data, an institution identifier associated with the mobile display device;
    determining a geographic location using the institution identifier; and
    assigning the institution identifier as the location of the ultrasound scanner.

6. The method of claim 5 further comprises:
    prior to identifying the one or more device features available for the ultrasound scanner, identifying one or more other devices associated with the institution identifier and determining one or more geographic locations associated with the one or more other devices; and
    generating a location error when at least one geographic location of the one or more locations is different, otherwise, proceeding to identify the one or more licensed features available for the ultrasound scanner based on the location.

7. The method of claim 2 further comprises:
    prior to identifying the one or more device features available for the ultrasound scanner based on the location data, determining a geographic location from the location data; and
    determining, from the geographic location, that refined location data is required for identifying the one or more device features and proceeding to refine the location data with additional location data from a secondary source.

8. The method of claim 2 wherein the at least one regional setting comprises the one or more device features available for the ultrasound scanner with a geographic location determined from the location data, the one or more device features being those approved by a regulatory authority for the geographic location.

9. The method of claim 1, wherein the connection is a wireless communication connection established at the mobile display device.

10. The method of claim 1, wherein the connection is a short-range wireless connection.

11. The method of claim 1 wherein the location data is selected from the group consisting of a country code and Global Positioning System (GPS) co-ordinates.

12. The method of claim 1 wherein configuring the at least one regional setting enables activation of the ultrasound scanner, the method additionally comprises:
    initiating an initial connection between the ultrasound scanner and the mobile display device;
    receiving, at the ultrasound scanner, the location data from the mobile display device via the initial connection; and
    establishing a communications connection at the ultrasound scanner based on the location data.

13. The method of claim 12, wherein the initial connection is a two-way radio communications protocol.

14. The method of claim 12 wherein establishing an activation connection at the ultrasound scanner based on the location data comprises:
    determining a geographic jurisdiction from the location data;
    determining a frequency band acceptable for the geographic location; and
    establishing the communication connection with the frequency band.

15. The method of claim 12, wherein establishing the communication connection at the ultrasound scanner based on the location data comprises:
    updating a configuration of the communication connection with the location data.

16. An ultrasound system for automatically configuring at least one regional setting on an ultrasound scanner, the system comprising:
    the ultrasound scanner; and
    a mobile display device comprising a processor that is communicatively connected to the ultrasound scanner and configured to:
        display images acquired by the ultrasound scanner:
        determine its location data and assign the location data to the ultrasound scanner;

configure the at least one regional setting on the ultrasound scanner based on the location data of the mobile display device assigned to the ultrasound scanner.

17. The system of claim 16 wherein the processor is additionally configured to identify one or more device features available for the ultrasound scanner based on the location data; and activate the one or more device features available for the ultrasound scanner.

18. The system of claim 17 wherein the one or more device features available for the ultrasound scanner based on the location data are those approved by a regulatory authority, within a geographic location determined by the location data.

19. The system of claim 16 wherein the mobile display device is communicatively connected to the ultrasound scanner by a wireless connection.

20. The system of claim 19 additionally comprising a workflow application on the mobile display device which provides the location data to a cloud-based server and, in response, receives from the cloud-based server an activation of one or more device features available for the ultrasound scanner, based on the location data.

\* \* \* \* \*